United States Patent

Cottingham

[11] Patent Number: 5,795,748
[45] Date of Patent: Aug. 18, 1998

[54] DNA MICROWELL DEVICE AND METHOD

[75] Inventor: Hugh V. Cottingham, Caldwell, N.J.

[73] Assignee: Becton Dickinson and Company, Franklin Lakes, N.J.

[21] Appl. No.: 721,372

[22] Filed: Sep. 26, 1996

[51] Int. Cl.$^6$ ............... G01N 21/29; G01N 21/64; G01N 21/27; C12P 19/34
[52] U.S. Cl. ............ 435/91.2; 422/82.05; 422/82.07; 422/82.09; 435/91.1
[58] Field of Search ............. 422/82.05, 82.07, 422/82.09; 435/91.2, 91.1

[56] References Cited

U.S. PATENT DOCUMENTS

| | | | |
|---|---|---|---|
| 5,047,206 | 9/1991 | Dombrowski | 422/56 |
| 5,229,297 | 7/1993 | Schnipelsky | 436/94 |
| 5,429,804 | 7/1995 | Sayles | 422/58 |
| 5,587,128 | 12/1996 | Wilding | 422/50 |
| 5,593,867 | 1/1997 | Walker | 435/91.2 |

FOREIGN PATENT DOCUMENTS

| | | |
|---|---|---|
| 0215419 | 3/1987 | European Pat. Off. |
| 0512334 | 11/1992 | European Pat. Off. |
| 0611598 | 8/1994 | European Pat. Off. |

*Primary Examiner*—Kenneth R. Horlick
*Assistant Examiner*—Joyce Tung
*Attorney, Agent, or Firm*—David W. Highet, Esq.

[57] ABSTRACT

An apparatus for carrying out a homogeneous nucleic acid amplification and nucleic acid assay on a liquid biological sample comprises a sample well and an optical window element which is received in the sample well. Opposed, spaced-apart surfaces of the optical window element and sample well define a capillary chamber into which a liquid biological sample is drawn by capillary force. By spreading the liquid biological sample into a thin film within the capillary chamber, head space is eliminated, heat transfer to the sample is maximized, and a large optical target is achieved to facilitate the detection step of the assay. The disclosed apparatus is particularly suited for use with homogeneous nucleic acid amplification and fluorescence polarization assays, but can also be used in connection with other types of biological and chemical processes.

21 Claims, 10 Drawing Sheets

DNA MICROWELL DEVICE AND METHOD

CROSS REFERENCE TO RELATED APPLICATION

Related subject matter is disclosed and claimed in co-pending, commonly-assigned U.S. patent application Ser. No. 08/527,253, filed by Hugh V. Cottingham on Sep. 12, 1995 and entitled "Device and Method for DNA Amplification and Assay", which application is expressly incorporated herein by reference.

FIELD OF THE INVENTION

The present invention relates generally to devices and methods for carrying out biological or chemical processes on liquid samples, and is particularly concerned with an integrated DNA amplification and assay device for carrying out homogeneous DNA fluorescence polarization assays.

BACKGROUND OF THE INVENTION

The processes of nucleic acid (DNA) amplification and subsequent nucleic acid probe assay are well known and have been implemented in a variety of formats. While these formats are highly effective, they are somewhat difficult to perform in the clinical laboratory. Generally, DNA amplification and assay reactions are performed sequentially on the sample to be assayed; that is, the DNA amplification reaction is first carried out to completion, and the DNA probe assay is then performed on the fully amplified sample. This is referred to as an end point assay.

One problem with end point assays is that the amplified DNA (amplicons) from the DNA amplification reaction must be physically transferred to the subsequent DNA probe assay. Because of the transfer, the potential exists for contaminating the laboratory environment with the DNA amplicons. In addition, the general risk of misidentifying a given sample or confusing it with other samples increases each time that a physical transfer of the sample takes place.

A number of proposals have been made for self-contained test units that are capable of carrying out an integrated nucleic acid amplification and assay on a liquid biological sample while the sample remains confined within the test unit. One such proposal, which employs an external roller to force sample and detection reagents through flexible compartments and passageways in the test unit, may be found in U.S. Pat. No. 5,229,297, to Paul N. Schnipelsky et al. Another example, in which the flow of sample and reagent liquids is controlled by centrifugal force rather than by a roller, is disclosed in co-pending, commonly-assigned U.S. patent application Ser. No. 08/277,553, filed by Hugh V. Cottingham on Jul. 19, 1994. The disadvantage of both of these proposals is that they require controlled fluid movements to be carried out within the test unit, and this renders the construction of the test unit somewhat more complex than might be desired.

In addition to the end point assays discussed above, homogenous methods of nucleic acid assay also exist. Homogeneous methods do not require the physical transfer of the amplified material to a separate assay site, but rather function simultaneously with the amplification reaction. Homogeneous methods are preferred because of their simplicity and reliability. Moreover, since homogeneous assays are usually performed in a closed tube, they have the advantage that there is little risk of contaminating other samples with their reaction products (amplicons). Examples of known homogenous assay methods include fluorescence polarization, fluorescence energy transfer and light absorbance.

Homogeneous nucleic acid assay methods generally employ a polypropylene "microtube" as the reaction container. This is less than satisfactory for several reasons. For example, a typical microtube has a volume of 200 µL, while a typical liquid biological sample to be assayed has a volume of 50 µL to 100 µL. This leaves a volume of air (known as "head space") above the liquid sample into which the reagents of the reaction can evaporate and subsequently condense. This is an undesirable condition and requires external heaters, applied to the top of the tube, to prevent condensation.

Another disadvantage of conventional microtubes is that nucleic acid amplification chemistries are very sensitive to starting temperature and require that a certain minimum temperature be achieved before the reaction is allowed to start. If this condition is not met, an undesired background reaction, caused by what is known as "mis-priming", will occur. The requirement for a certain minimum starting temperature is known as a "hot start".

When the homogeneous assay method relies upon fluorescence polarization, polypropylene microtubes cannot be used and glass reaction containers must be substituted. This is due to the fact that most plastic processing methods, such as injection molding and thermoforming, create stresses in the material of the finished part. These stresses have random polarization effects, and interfere with the transmission of polarized light that is required for a fluorescence polarization assay.

In view of the foregoing, it is an object of the present invention to provide a low-volume reaction device that has virtually no head space, does not require that external heaters be provided on top of the device, and is not subject to evaporation and condensation of the liquid biological sample contained within the device.

It is another object of the present invention to provide a reaction device and method that can achieve a "shot start" of a nucleic acid amplification reaction, thereby avoiding invalid assay results due to mis-priming.

It is a further object of the present invention to provide a reaction device that can be constructed largely or entirely of plastic materials, but that has the optical properties necessary for carrying out a fluorescence polarization assay.

It is a further object of the present invention to provide an integrated nucleic acid amplification and assay device in which all of the reagents needed for both amplification and assay are contained, in dried form, within the device, so that the addition of a liquid biological sample is all that is needed to carry out a nucleic acid assay.

It is a still further object of the present invention to provide an integrated nucleic acid amplification and assay device that can be sealed after the introduction of a liquid biological sample, thereby preventing amplicon contamination of the laboratory environment.

SUMMARY OF THE INVENTION

In accordance with a preferred embodiment of the present invention, the disadvantages and limitations of the prior art are substantially avoided by providing an integrated nucleic acid amplification and assay device which comprises a sample well, an optical window element that is receivable in the sample well, and a closure device. The optical window element is held in the sample well in a manner such that a thin capillary chamber is defined between an inner surface of the window element and a confronting interior surface of the sample well. Dried nucleic acid amplification and assay reagents are provided in the capillary chamber. In use, a liquid biological sample is drawn by capillary force into the capillary chamber, and the closure device is then used to seal the capillary chamber. Within the capillary chamber, the liquid biological sample is spread into a thin layer that can be heated relatively quickly, thereby avoiding mis-priming of the amplification reaction. An optical detection step may be carried out through the optical window element, without the need to remove the liquid sample from the reaction device.

In one aspect, therefore, the present invention is directed to an apparatus for carrying out a biological or chemical reaction on a liquid sample. The apparatus includes a sample well having an interior portion defined by a substantially flat, upwardly facing bottom wall surface and upstanding side wall surfaces, and an optical window element which is receivable in the sample well. The optical window element has a substantially flat, downwardly facing bottom surface which is maintained in opposed, spaced-apart relationship with the bottom wall surface of the sample well to define a capillary chamber therebetween. An opening is provided for allowing a liquid sample to be introduced into the capillary chamber and to be drawn into the capillary chamber by capillary action. A closure device is provided for sealing the opening after a liquid sample has been introduced into the capillary chamber.

In another aspect, the present invention is directed to an apparatus for carrying out a homogeneous nucleic acid amplification and nucleic acid assay on a liquid biological sample. The apparatus comprises a sample well having an interior portion defined by a substantially flat, upwardly-facing bottom wall surface and upstanding side wall surfaces, and an optical window element which is receivable in the sample well. The optical window element has a substantially flat, downwardly-facing bottom surface which is maintained in opposed, spacedapart relationship with the bottom wall surface of the sample well to define a capillary chamber therebetween. An opening is provided to allow a liquid biological sample to be introduced into the capillary chamber and to be drawn into the capillary chamber by capillary action. A closure device is provided for sealing the opening after a liquid biological sample has been introduced into the capillary chamber. Dried homogeneous nucleic acid amplification and assay reagents are adhered to the interior of the capillary chamber for reacting with the liquid biological sample in the chamber.

In a still further aspect, the present invention is directed to a method for carrying out an integrated nucleic acid amplification and homogeneous nucleic acid fluorescence polarization assay on a liquid biological sample. The method comprises the steps of providing a sample well having a substantially flat, upwardly-facing, bottom interior surface; inserting into the sample well an optical window element having a substantially flat, downwardly facing bottom surface; maintaining the bottom surface of the optical window element in opposed, spaced-apart relationship with the bottom interior surface of the sample well to define a capillary chamber therebetween; introducing a liquid biological sample into the capillary chamber; bringing the liquid biological sample into contact with a dried nucleic acid amplification reagent and a dried homogeneous nucleic acid fluorescence polarization assay reagent in the capillary chamber; sealing the capillary chamber; incubating the sample well to allow the liquid biological sample to react with the nucleic acid amplification reagent and the nucleic acid fluorescence polarization assay reagent; and detecting fluorescence polarization in the liquid biological sample through the optical window element.

BRIEF DESCRIPTION OF THE DRAWINGS

The various objects, advantages and novel features of the invention will be more readily appreciated from the following detailed description when read in conjunction with the appended drawing figures, in which.

Throughout the drawings, like reference numerals will be understood to refer to like parts and components.

DETAILED DESCRIPTION OF THE PREFERRED EMBODIMENT

Figure 1:
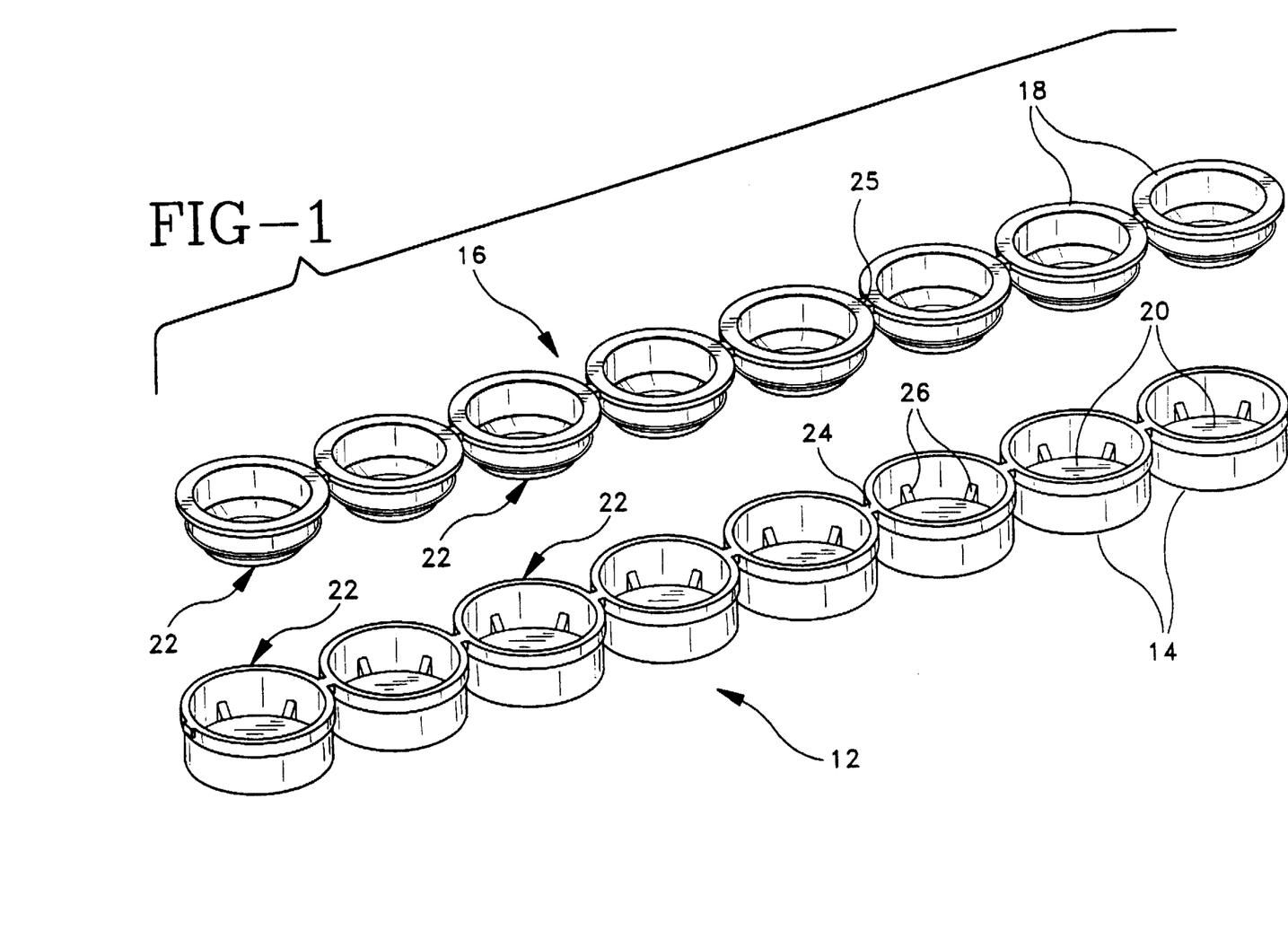
FIG. 1 is an exploded view illustrating a strip of eight connected DNA sample wells and a strip of eight connected seals for the sample wells, together forming a series of sample well assemblies constructed in accordance with a preferred embodiment of the present invention.

A multiple-well apparatus 10 adapted for carrying out an integrated nucleic acid amplification and assay procedure in accordance with a preferred embodiment of the present invention is illustrated in FIG. 1. The apparatus 10 comprises a first strip 12 of eight connected sample wells 14, and a second strip 16 of eight connected seals or caps 18. Each sample well 14, when combined with its corresponding seal 18 and with an inserted optical window element 20, forms a sample well assembly 22 in which an integrated nucleic acid amplification and assay procedure can be carried out on a discrete liquid biological sample. The individual sample wells 14 in the strip 12 are connected to each other in a linear fashion by means of integral tabs 24, which can be broken by the user to subdivide the strip 12 if fewer than eight samples are to be assayed. Similar breakable tabs 25 are used to connect the seals 18 in a linear arrangement as shown. The strip 12 of sample wells 14 is preferably formed in one piece by injection molding, using a suitable plastic material such as polypropylene. The strip 16 of seals 18 may be formed in the same manner, and is preferably made of the same material. In the preferred embodiment, the individual sample wells 14 are generally cylindrical in shape with an outside diameter of approximately 0.320 inch, an outside height of approximately 0.175 inch and a wall thickness of approximately 0.015 inch. The center-to-center distance from one sample well 14 to the next (and from one seal 18 to the next) is approximately 0.354 inch.

As shown in FIG. 1, each sample well 14 contains an inserted optical window element 20 in the form of a transparent circular disk supported by a plurality of ribs 26 which are spaced circumferentially around the interior of the sample well. As will be described in more detail hereinafter, the lower surface of each optical window element 20 is spaced from the bottom wall of the corresponding sample well 14 by a small distance (preferably about 0.020 inch) to create a capillary chamber within the bottom of the sample well. A liquid biological sample to be assayed is introduced into the capillary chamber, preferably through an annular gap or opening which exists between the outer edges of the optical window element 20 and the vertical interior wall surfaces of the sample well 14. One of the seals 18 is then fitted to the sample well 14 to close this opening, and the liquid biological sample is allowed to react with dried nucleic acid amplification and assay reagents contained within the capillary chamber. After the reaction has progressed to a point at which detection can begin, an optical detection step is carried out through the optical window element 20 without the need to remove the liquid biological sample from the sealed sample well 14. In this manner, the possibility of cross-contamination with other liquid biological samples is minimized.

Figure 2A:
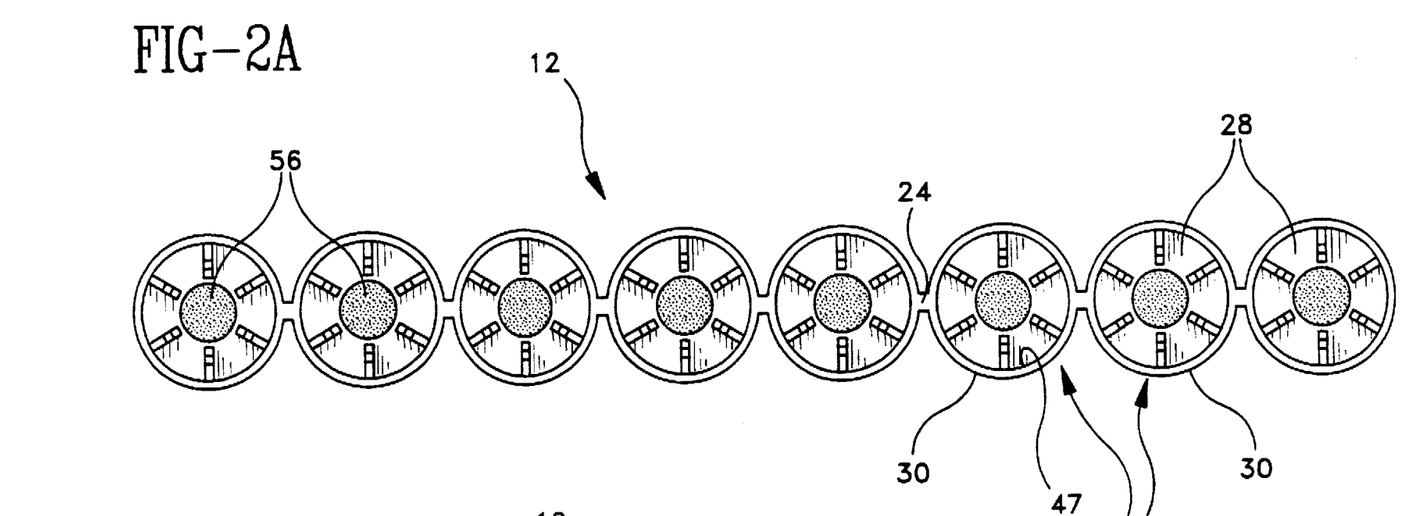
FIGS. 2A, 2B and 2C are top, side sectional and bottom views, respectively, of the strip of connected DNA sample wells.
Figure 2B:
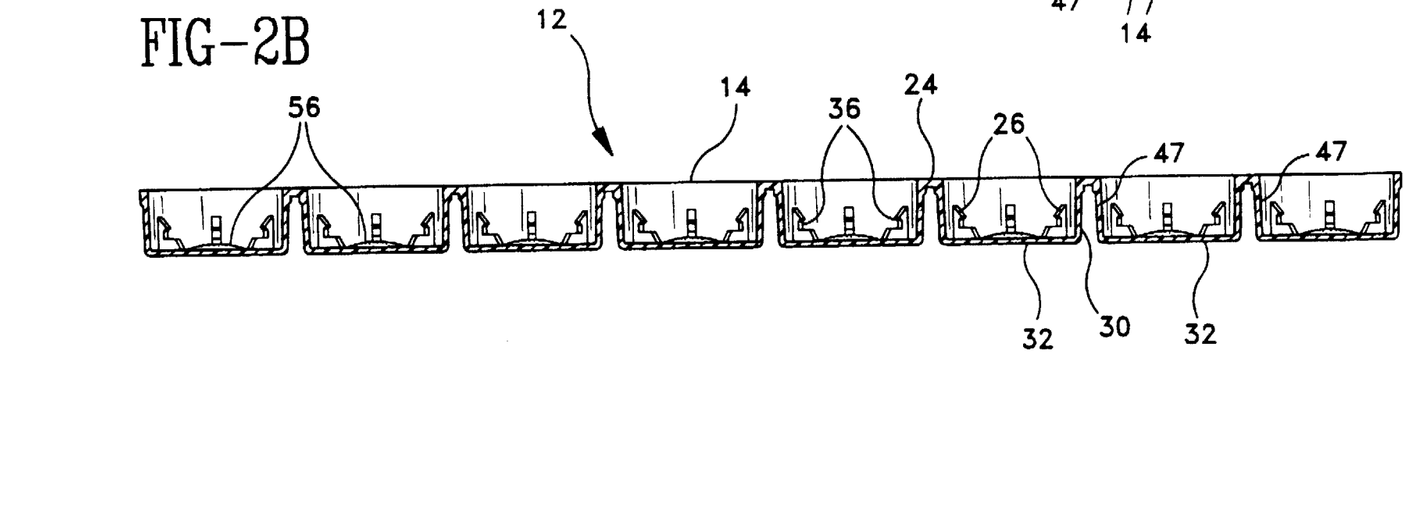
Figure 2C:
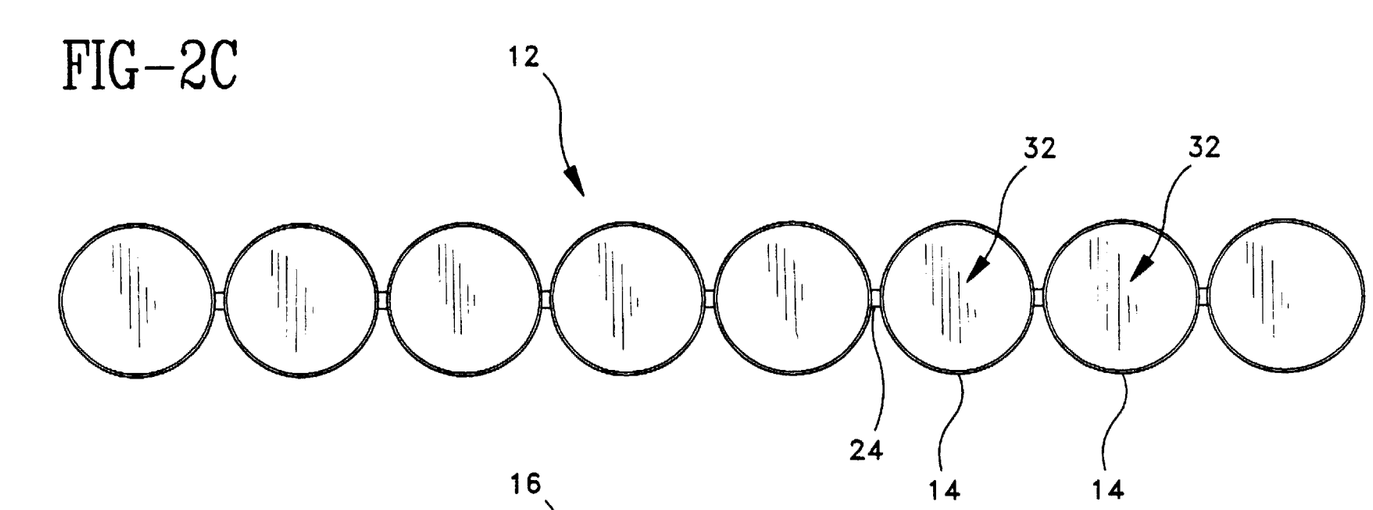

The detailed configuration of the sample wells 14 is illustrated in FIGS. 2A, 2B and 2C. In the preferred embodiment, each sample well 14 is generally cylindrical in shape, with a circular top opening 28, upstanding cylindrical side walls 30, and a flat circular bottom wall 32. Spaced equidistantly around the interior circumference of the sample well 14 are six wedge-shaped ribs or spacers 26 with notches 36 facing toward the center of the sample well. In the preferred embodiment, the ribs 26 are carried by the bottom wall 32 of the sample well 14, and are formed integrally therewith during the plastic molding operation. As will be described hereinafter, the notched ribs 26 serve to locate and retain the optical window element 20 at the proper location within the sample well 14.

Figure 3A:
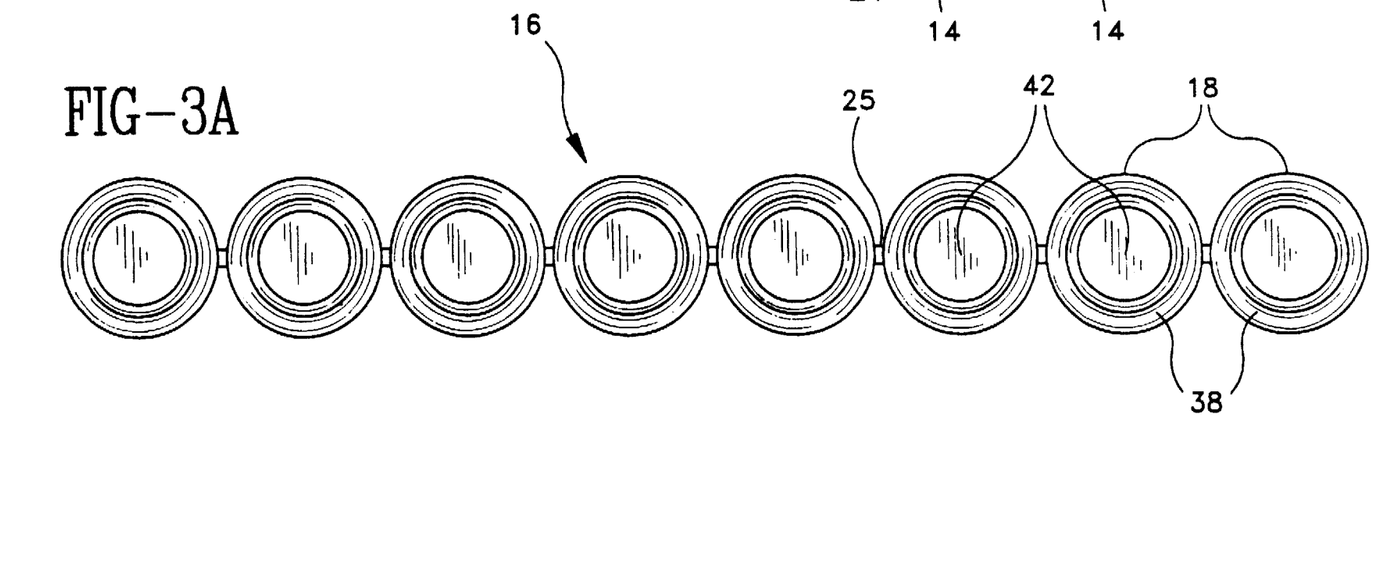
FIGS. 3A, 3B and 3C are top, side sectional and bottom views, respectively, of the strip of connected seals for the DNA sample wells.
Figure 3B:
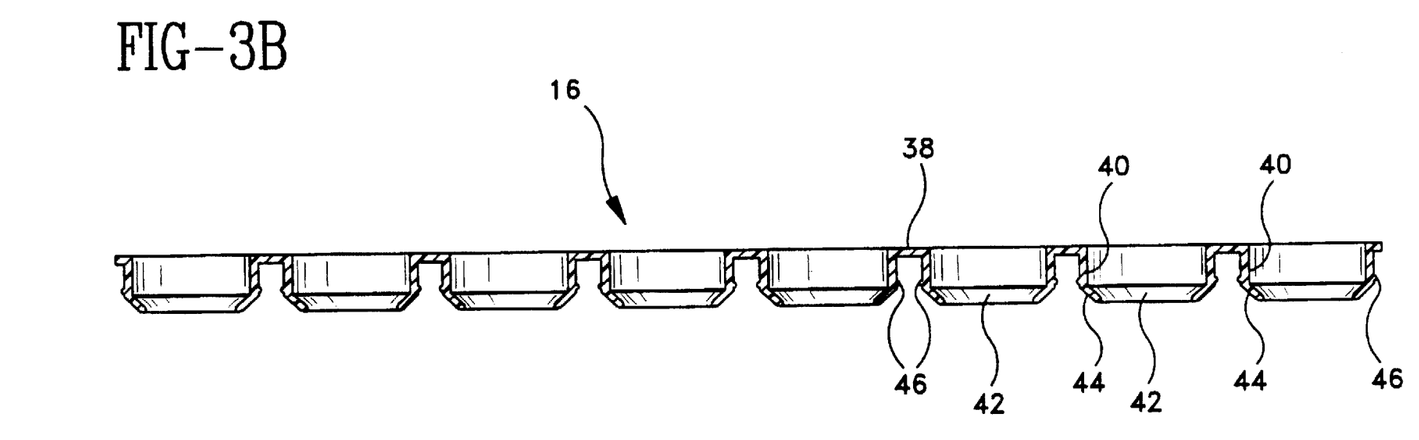
Figure 3C:
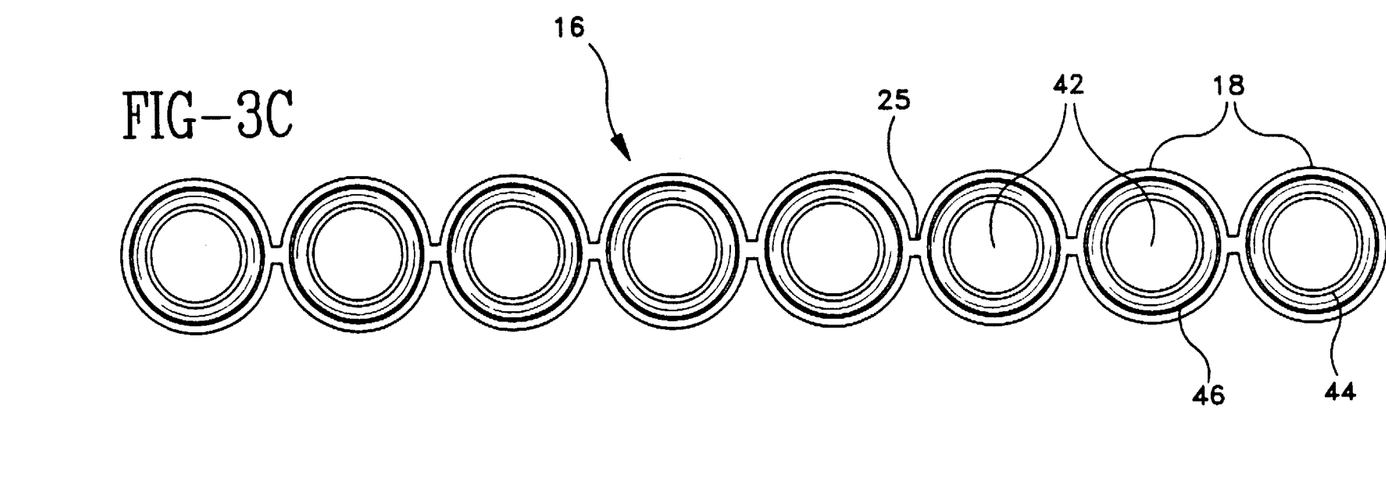

The details of the seals or caps 18 are shown in FIGS. 3A, 3B and 3C. Each seal 18 is generally annular in shape, with an upwardly-facing circular rim or flange 38, downwardly extending cylindrical side walls 40, and a central circular aperture 42. Surrounding the lower opening of the aperture 42 is a downwardly extending, frusto-conical extension 44 which is formed integrally with the side walls 40 and tapers inwardly toward the central axis of the annular seal 18. As will be described shortly, the lower edge of the extension 44 is brought into contact with the periphery of the optical window element 20 when the sample well assembly 22 is fully assembled, in order to seal the capillary chamber below the optical window element 20 after a liquid biological sample has been introduced into the capillary chamber. The capillary chamber is also sealed by means of a circular sealing ring 46 that is formed around the outside of the cylindrical side walls 40 of the seal 18. The sealing ring 46 frictionally engages the interior side wall surfaces 47 of the sample well 14 (visible in FIGS. 2A and 2B) in order to hold the seal 18 in place on the sample well.

Figure 4A:
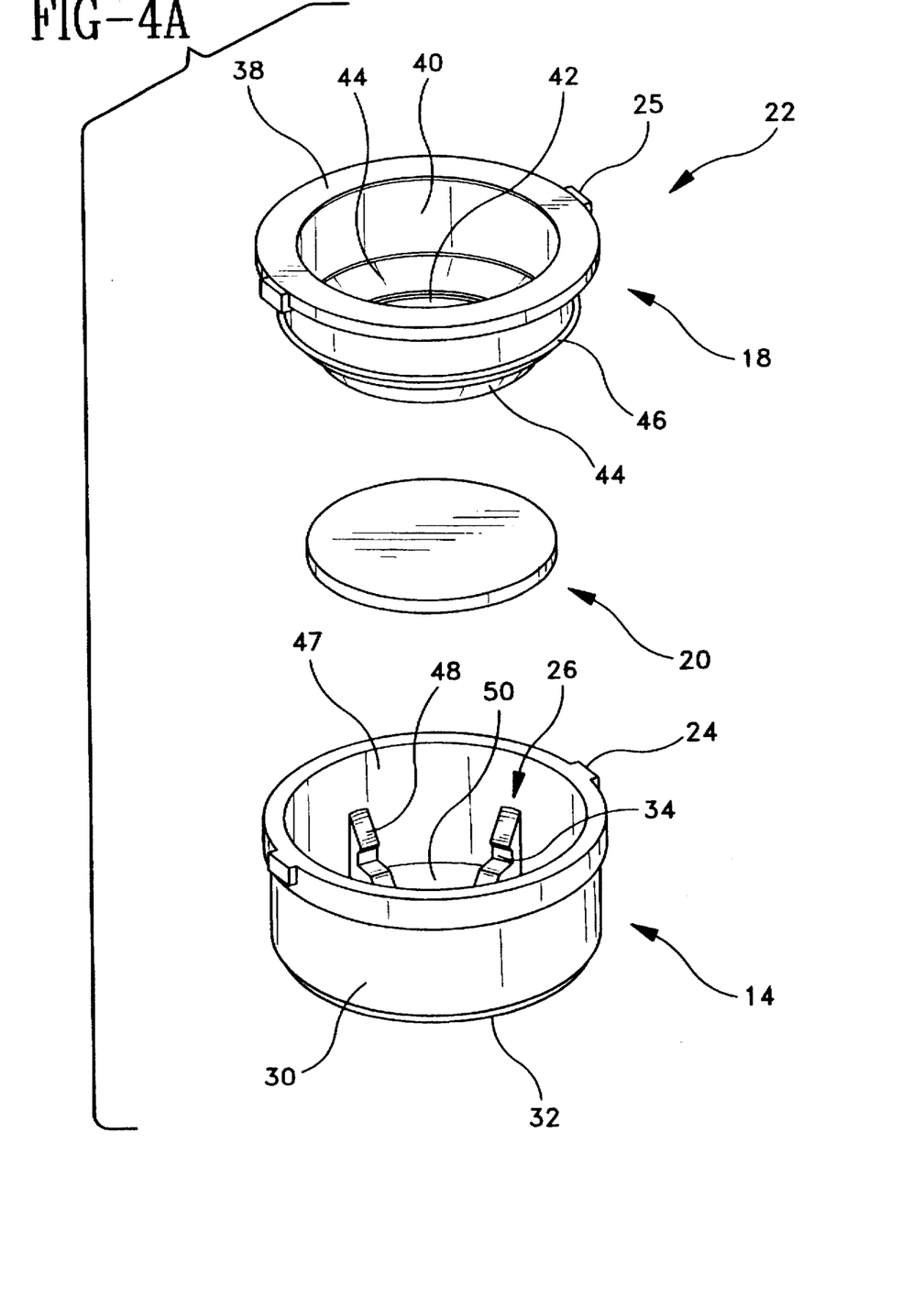
FIGS. 4A and 4B are exploded and assembled views, respectively, of a single DNA sample well assembly.
Figure 4B:
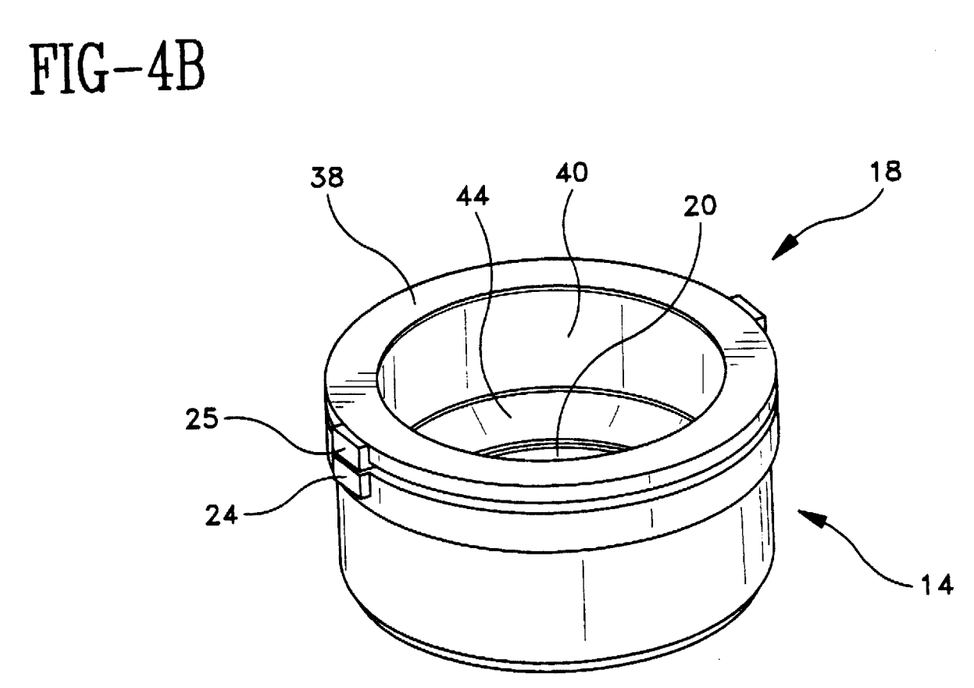

The manner in which each of the sample well assemblies 22 is assembled prior to carrying out an integrated nucleic acid amplification and assay procedure is illustrated in FIGS. 4A and 4B. The optical window element 20 is inserted into the sample well 14 and is received and retained in the notches 34 formed in the radially arranged ribs 26. (This is preferably—although not necessarily—done during the manufacturing process, so that the sample well 14 reaches the user with the optical window element 20 already installed.) The plastic material of which the ribs 26 and sample well 14 are made is sufficiently resilient to allow the ribs 26 to flex or move slightly as the optical window element 20 is inserted into the notches 34, allowing for a positive "snap" engagement between the optical window element 20 and the notches 34. The upwardly facing surfaces 48 of the ribs 26 are preferably inclined downwardly toward the center of the sample well 14 at an angle of about 45°, as shown, in order to provide guide surfaces for directing the edges of the optical window element 20 into the notches 34.

After the optical window element 20 has been inserted into the sample well 14, a liquid biological sample is introduced into the capillary chamber located below the optical window element 20, as will be described below. The seal 18 is then placed on the sample well in order to seal the capillary chamber. When the seal 18 is in place, the sealing ring 46 is in frictional engagement with the interior side walls 47 of the sample well, and the lower edge of the extension 44 is in contact with the peripheral portion of the optical window element 20. The fully assembled condition of the sample well assembly 22 is shown in FIG. 4B.

Figure 5A:
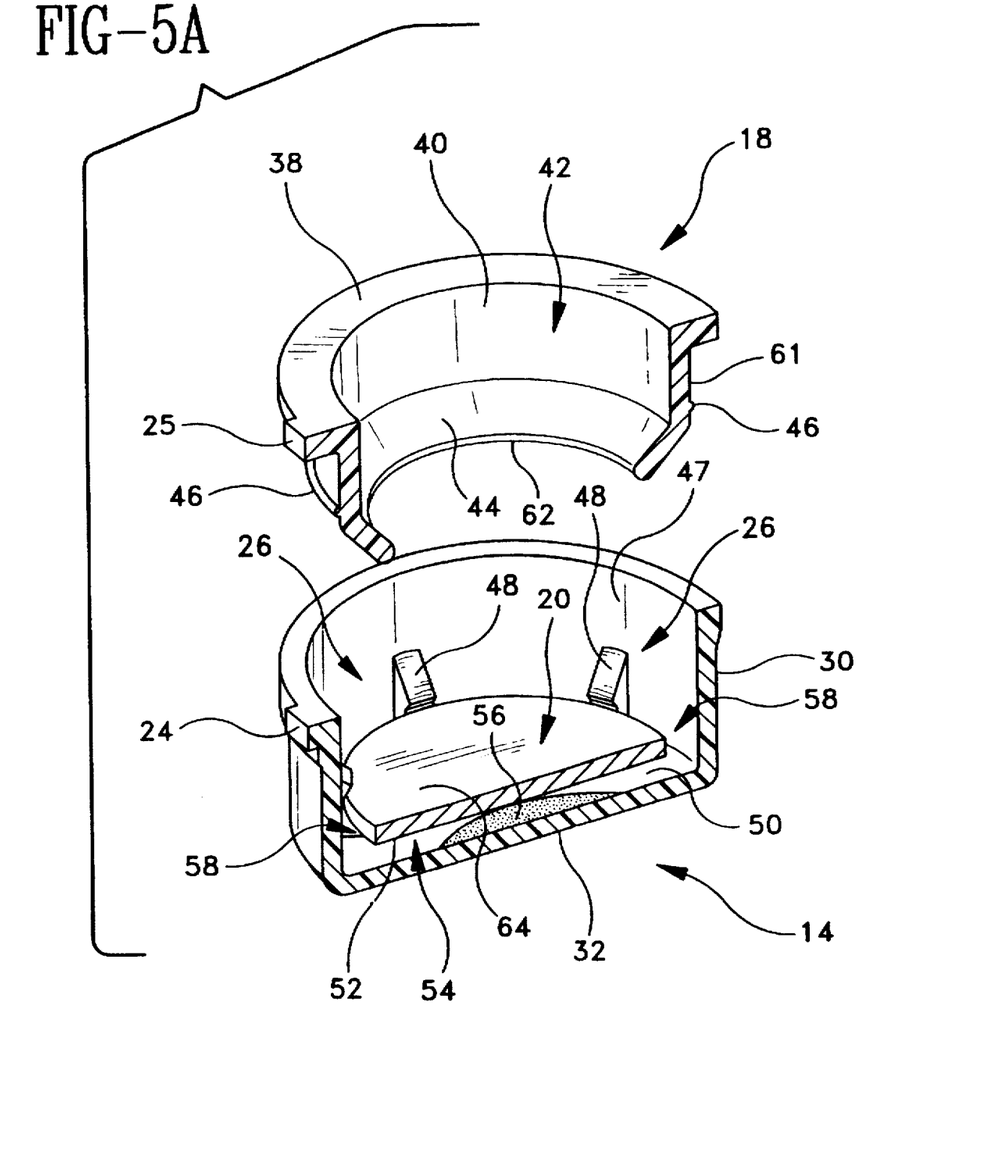
FIGS. 5A and 5B are exploded and assembled sectional views, respectively, of a single DNA sample well assembly, with the optical window element of the assembly shown installed in the sample well in both views.
Figure 5B:
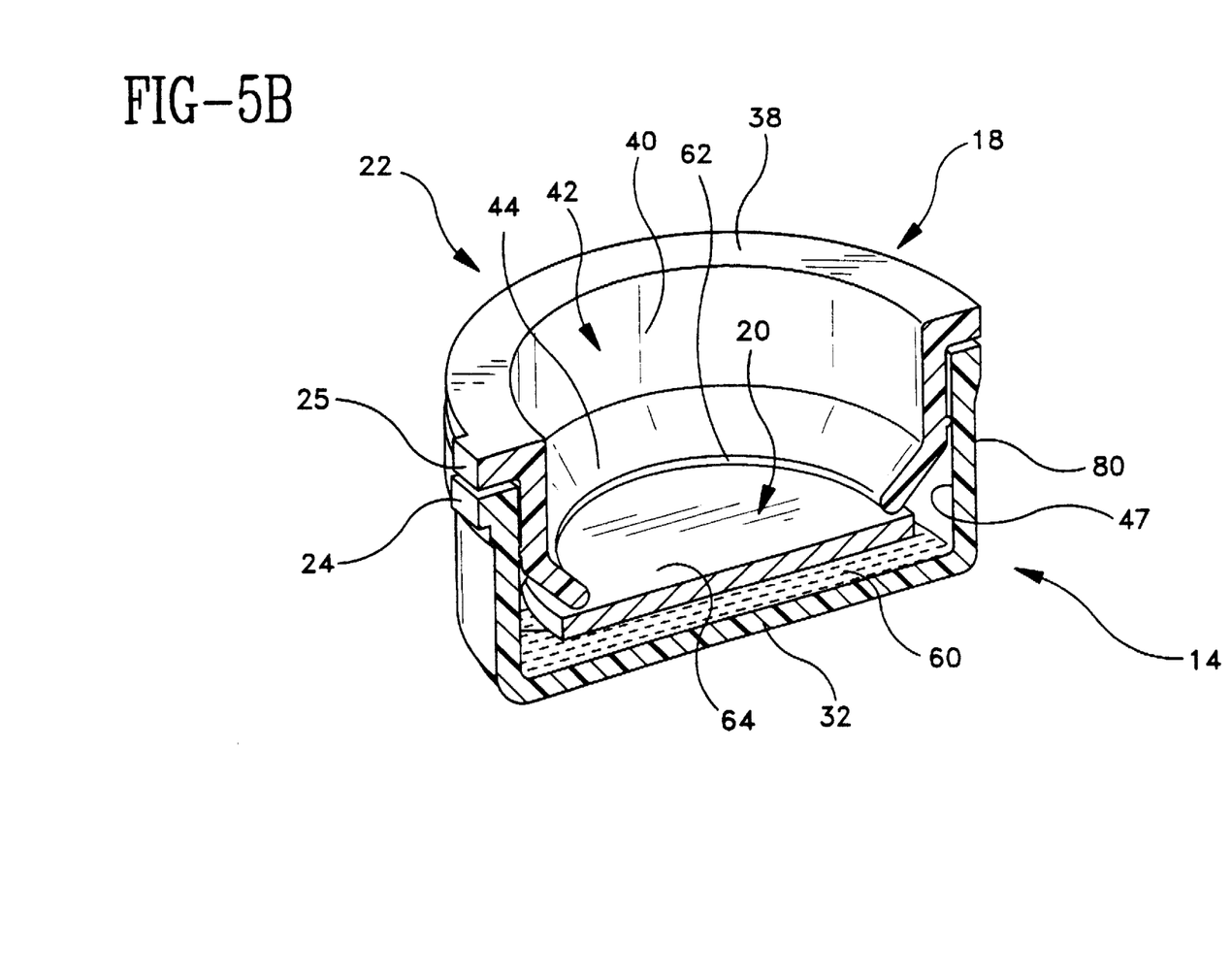

FIGS. 5A and 5B are sectional views illustrating the internal configuration of the sample well assembly 22, with the seal 18 shown removed in FIG. 5A and fully installed in FIG. 5B. As best seen in FIG. 5A, the optical window element 20 is held by the notched ribs 26 in a parallel relationship with the bottom wall 32 of the sample well 14, with a uniform gap (preferably about 0.020 inch in height) being maintained between the upwardly-facing surface 50 of the wall 32 and the confronting, downwardly-facing surface 52 of the optical window element 20. This gap or space defines a cylindrical or disk-shaped capillary chamber 54 between the surfaces 50 and 52. A spot 56 containing dried homogeneous nucleic acid amplification and fluorescence polarization assay reagents is affixed to the surface 50 at a central position within the capillary chamber 54. When a liquid biological sample is introduced into the capillary chamber 54, the reagents in the dried spot 56 are rehydrated by the sample to initiate the desired amplification and assay reactions. In order to allow for the introduction of a liquid biological sample into the capillary chamber 54, the sample well 14 and the optical window element 20 are dimensioned such that an annular gap 58 of approximately 0.020 inch is provided between the outer periphery of the optical window element 20 and the confronting interior wall surfaces 47 of the sample well 14. In the preferred embodiment, this is accomplished by forming the sample well 14 with an inside diameter of approximately 0.290 inch, and by forming the optical window element 20 with an outside diameter of approximately 0.250 inch.

In FIG. 5B, the sample well assembly 22 is shown fully assembled with a liquid biological sample 60 present within the capillary chamber 54. The liquid biological sample 60 substantially fills the capillary chamber 54, which has a volume of about 20 μL. By virtue of the narrow spacing between the confronting surfaces 50 and 52 of the bottom wall 32 and optical window element 20, respectively, the liquid biological sample is drawn into the chamber 54 by capillary forces and is spread into a thin film or disk having a height (thickness) of about 0.020 inch and a diameter of about 0.250 inch. In this configuration, the liquid biological sample 60 has a large surface area relative to its volume and equilibrates to the temperature of the sample well 14 in a matter of a few seconds. In addition, by spreading the liquid biological sample into a thin film, a large optical target is achieved relative to the volume of the sample. This is desirable when an optical detection step is performed, as in the case of a fluorescence polarization assay.

The manner in which the seal 18 closes off the capillary chamber 54 will be evident from FIG. 5B. Closure of the capillary chamber 54 occurs along two separate zones, one defined by the circular line of contact between the sealing ring 46 and the internal vertical walls 47 of the sample well 14, and the other defined by the circular line of contact between the lower edge 62 of the frusto-conical extension 44 and the upper surface 64 of the optical window element 20. The sealing ring 46 prevents the liquid sample 60 from passing between the internal walls 47 of the sample well 14 and the external walls 61 of the seal 18, and also serves to frictionally retain the seal 18 within the sample well 14. The lower edge 62 of the extension 44 provides a similar sealing zone between the seal 18 and the optical window element 20, and also assists in retaining the optical window element 20 within the notches 34 of the ribs 26. In addition, the aperture 42 in the seal 18 provides a free optical path to the optical window element 20 when the sample well assembly 22 is fully assembled, thereby allowing an optical detection step to be carried out on the liquid biological sample 60 while the sample remains confined within the capillary chamber 54.

Figures 6A, 6B:
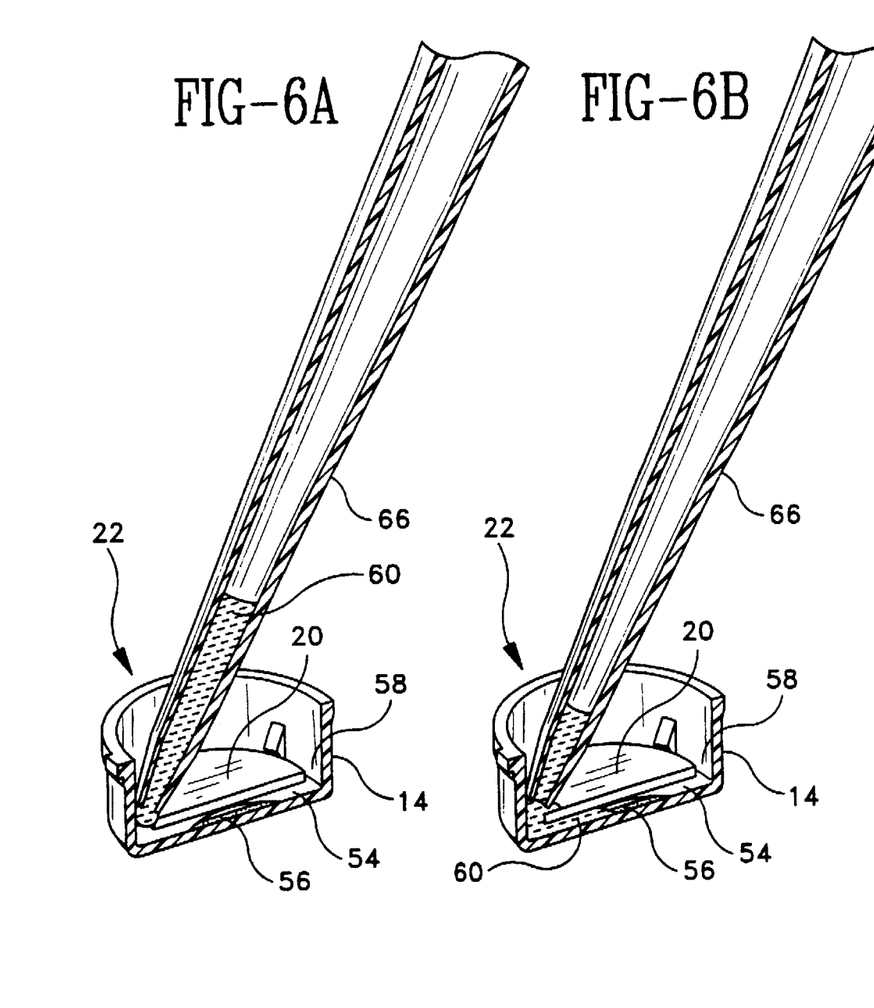
FIGS. 6A, 6B and 6C are sequential sectional views illustrating the manner in which a liquid biological sample is introduced into a partially assembled DNA sample well assembly by means of a pipette.
Figure 6C:
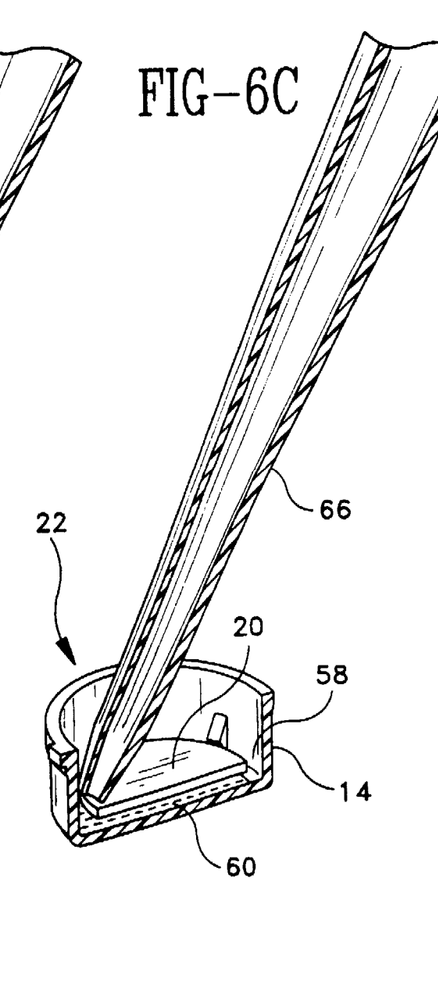

FIGS. 6A, 6B and 6C illustrate the manner in which a liquid biological sample 60 is introduced into the capillary chamber 54 of a sample well assembly 22. Prior to introducing the liquid biological sample into the capillary chamber, the sample well assembly 22 has been partially assembled by inserting the optical window element 20 into the notched ribs 26 of the sample Nvell 14. A pipette 66 containing the liquid biological sample 60 to be assayed (typically consisting of a prepared blood sample or other body fluid sample that is to be tested for a specific pathogen) is positioned with its opening just above the gap 58 between the periphery of the optical window element 20 and the interior vertical walls 47 of the sample well 14, as shown in FIG. 6A. The pipette 66 will typically be of the disposable type and may be carried either by a manual pipetting apparatus or by an automated (robotic) pipetting apparatus. In either case, the pipetting apparatus is operated to dispense the liquid biological sample 60 from the pipette 66 onto the top surface of the optical window element 20 in the region near the gap 58. As this occurs, capillary forces automatically draw a measured volume of the liquid sample 60 into the gap 58 and into the capillary chamber 54 below the optical window element 20, as shown in FIG. 6B. The capillary forces cause the liquid biological sample 60 to be spread into a thin film disk which substantially fills the capillary chamber 54 with no head space, as illustrated in FIG. 6C. As noted above, this configuration is advantageous not only because it provides efficient heat transfer between the sample well 14 and the liquid sample 60, but also because it affords a large optical target for subsequent detection.

Figure 7A:
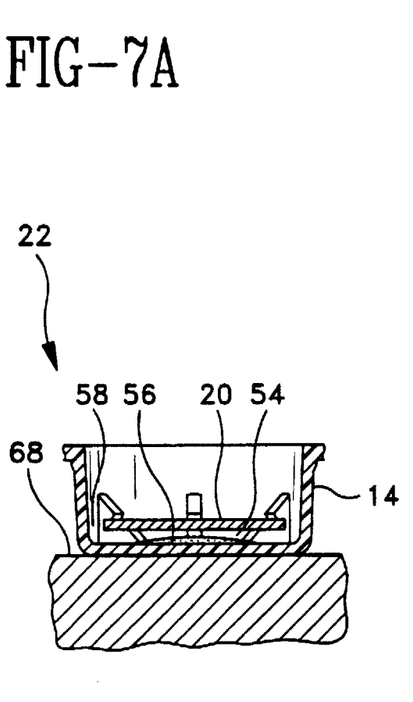
FIGS. 7A, 7B and 7C are sequential sectional views illustrating the manner in which the DNA sample well assembly of the present invention may be used to carry out a nucleic acid amplification and homogeneous nucleic acid fluorescence polarization assay using dried reagents affixed within the reaction area of the assembly.
Figure 7B:
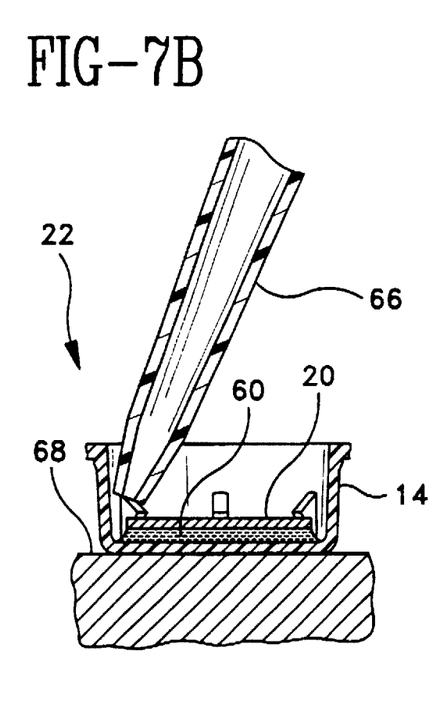
Figure 7C:
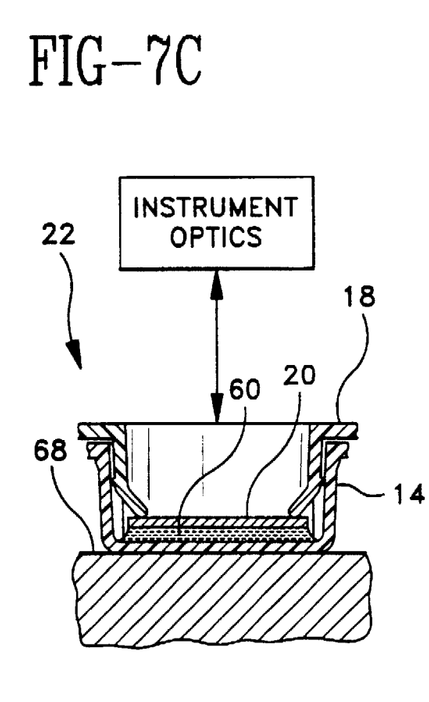

FIGS. 7A, 7B and 7C illustrate the manner in which a sample well assembly 22 constructed in accordance with the present invention can be used to carry out a homogeneous nucleic acid amplification and assay procedure on a liquid biological sample. In FIG. 7A, an empty sample well 14 containing an optical window element 20 and dried reagents 56 is placed on a heating platen 68. The heating platen 68 is operated to pre-heat the sample well 14 to a temperature (typically between 25° C. and 75° C.) which is suitable for a homogeneous nucleic acid amplification and assay procedure. The pre-heating step is carried out for a time interval sufficient to allow the empty sample well 14 to equilibrate to a temperature approximately equal to that of the heating platen 68. After this has occurred, a liquid biological sample is introduced into the capillary chamber 54 using a pipette 66, as illustrated in FIG. 7B. This is preferably accomplished by positioning the open end of the pipette 66 immediately above the gap 58, as illustrated in FIG. 7B, and then dispensing the liquid sample 60 directly into the gap 58.

After the liquid sample 60 has filled the capillary chamber 54, the pipette 56 is withdrawn and a seal 18 is placed on the sample well 14. The liquid biological sample 60 rehydrates the dried nucleic acid amplification and assay reagents within the dried spot 56, and a homogeneous amplification and assay reaction occurs while the sample 60 is contained within the capillary chamber 54. Due to the thinness of the capillary chamber 54 and the large surface area with which the liquid biological sample 60 comes into contact, the sample 60 heats up within a few seconds of being pipetted into the chamber 54 to the optimum temperature desired for DNA amplification. Thus, by the time the dried reagents 56 dissolve and diffuse throughout the liquid biological sample 60 to begin "priming" the DNA amplification, the reagents are already up to the optimum temperature. In this way, a "hot start" of the DNA amplification reaction is achieved. After the "hot start" occurs, the heating platen 68 continues to maintain the liquid biological sample 60 at a temperature (typically between 25° C. and 75° C.) that is suitable for the homogeneous amplification and assay reactions. As the homogeneous amplification and assay reactions occur, their progress is monitored in real time by suitable optical detection apparatus 70. Depending upon the nature of the assay reaction, the apparatus 70 may detect fluorescence polarization, fluorescence energy transfer, light absorbance, or any other optical response or characteristic of the liquid biological sample 60. Various types of apparatus 70 which may be used for this purpose, such as microplate fluorometers, are known in the art and need not be described in detail. Reference is made to the aforementioned co-pending application Ser. No. 08/527,253 for a description of specific detection methods that may be employed when the assay is of the fluorescence polarization type.

In the case where the sample well assembly 22 is used to carry out a fluorescence polarization assay, the optical window element 20 is preferably made of a transparent material that does not interfere with the transmission of polarized light. Examples of such materials include cellulose acetate butyrate (CAB), triacetate cellulose (TAC), and glass. Polarized light will pass through these materials and retain its polarization. The sample well assembly 22 can, if desired, be configured for use in a confocal polarization detection method as described in co-pending application Ser. No. 08/527,253. In this method, the polarizer for the excitation beam is also used as the polarizer for the fluorescence emitted by the sample. This avoids the need to provide polarizing elements in the measuring instrument, thereby allowing standard microplate fluorometers to be used in a fluorescence polarization assay. To employ the confocal method, the optical window element 20 is made of a light-polarizing material so that it will serve to polarize both the excitation beam from the detection apparatus 70 and the fluorescence emitted by the liquid biological sample 60. Exemplary light-polarizing materials include laminates or "sandwiches" in which a layer of polarizing polymeric film, such as polyvinyl alcohol (PVA), is disposed between layers of CAB, TAC or glass.

In the preferred embodiment, the dried reagent spot 56 contains both DNA amplification and homogeneous DNA assay reagents, the latter preferably consisting of fluorescence polarization assay reagents. Examples of suitable DNA amplification and DNA fluorescence polarization assay reagents are disclosed in copending U.S. patent application Ser. No. 08/311,474, filed by G. Terrance Walker et al on Sep. 23, 1994 and entitled "Fluorescence Polarization Detection of Nucleic Acid Amplification", now U.S. Pat. No. 5,593,867, said application being expressly incorporated herein by reference. The chemical reagents in the dried spot 56 are carried in a readily soluble matrix, such a trehalose or another carbohydrate. These reagents will spontaneously re-suspend when exposed to an aqueous sample introduced into the capillary chamber 54. It will be understood that more than one dried reagent spot 56 may be provided in the capillary chamber 54 if desired, as for example by providing the amplification reagents in one spot and the assay reagents in a different spot. In the case of a homogeneous DNA amplification and assay, however, the reagent spots (if separated) should be positioned in such a way that they are dissolved by the liquid biological sample 60 at essentially the same time.

The foregoing is illustrative of the present invention, and is not to be construed to be limiting thereof, as numerous alternatives to the devices and methods which incorporate the present invention will be apparent to those skilled in the art. The invention is accordingly defined by the following claims with equivalents of the claims to be included therein.

That which is claimed is:

1. An apparatus for carrying out a biological or chemical reaction on a liquid sample, comprising:
   a plurality of connected sample wells for receiving a liquid sample, each of said sample wells having an interior portion defined by a substantially flat, upwardly facing bottom wall surface and upstanding side wall surfaces;
   an optical window element receivable in each of said sample wells, said optical window element having a circumferential edge and a substantially flat, downwardly facing bottom surface which is maintained in opposed, spaced-apart relationship with the bottom wall surface of each of said sample wells to define a capillary chamber therebetween;
   an opening between the circumferential edge of said optical window element and a confronting interior side wall surface of each of said sample wells for allowing a liquid sample to be introduced into said capillary chamber and to be drawn into said chamber by capillary action; and
   a closure device for sealing said opening after a liquid sample has been introduced into said capillary chamber.

2. An apparatus as claimed in claim 1, wherein said optical window element is maintained in said opposed, spaced-apart relationship with the bottom wall surface of said sample well by at least one spacer carried by an interior wall surface of said sample well.

3. An apparatus as claimed in claim 2, wherein said spacer is integral with said sample well.

4. An apparatus as claimed in claim 2, wherein said spacer includes an engagement portion for engaging said optical window element.

5. An apparatus as claimed in claim 2, wherein said sample well and said optical window element are both substantially cylindrical in shape, and wherein said spacer comprises one of a plurality of spacers disposed around the circumference of the interior portion of said sample well.

6. An apparatus as claimed in claim 1, wherein said optical window element and the interior portion of said sample well have substantially the same shape when viewed from above.

7. An apparatus as claimed in claim 6, wherein said optical window element and the interior portion of said sample well are both substantially circular in shape when viewed from above, and wherein said gap is substantially annular.

8. An apparatus as claimed in claim 1, wherein said closure device is receivable by said sample well in at least partially overlying relationship with said optical window element to seal said opening.

9. An apparatus as claimed in claim 8, wherein said sample well, said optical window element and said closure device are all substantially circular in shape when viewed from above, said closure device overlying said optical window element and having a central aperture for exposing a portion of said optical window element.

10. An apparatus as claimed in claim 1, further comprising a reagent affixed within said capillary chamber for reacting with a liquid sample introduced into said capillary chamber.

11. An apparatus for carrying out a homogeneous nucleic acid amplification and nucleic acid assay on a liquid biological sample, comprising:
    a sample well for receiving a liquid biological sample, said sample well having an interior portion defined by a substantially flat, upwardly facing bottom wall surface and upstanding side wall surfaces;
    an optical window element receivable in said sample well, said optical window element having a circumferential edge and a substantially flat, downwardly facing bottom surface which is maintained in opposed, spaced-apart relationship with the bottom wall surface of said sample well to define a capillary chamber therebetween;
    an opening between the circumferential edge of said optical window element and a confronting interior side wall surface of said sample well for allowing a liquid sample to be introduced into said capillary chamber and to be drawn into said capillary chamber by capillary action;
    a closure device receivable in said opening for sealing said opening after a liquid biological sample has been introduced into said capillary chamber; and
    a dried nucleic acid amplification reagent for amplifying a target nucleic acid sequence in said liquid biological sample and a dried homogeneous nucleic acid assay reagent for providing an optically detectable indication of the presence of amplified target nucleic acid sequences in said liquid biological sample, said amplification and assay reagents being adhered to the interior of said capillary chamber for reacting with said liquid biological sample.

12. An apparatus as claimed in claim 11, wherein said dried nucleic acid amplification reagent and said dried nucleic acid assay reagent are provided in the form of a single spot adhered to an internal surface of said capillary chamber.

13. An apparatus as claimed in claim 11, wherein said dried nucleic acid assay reagent comprises a fluorescence polarization assay reagent, and wherein said optical window element is made of a material that does not interfere with the transmission of polarized light.

14. An apparatus as claimed in claim 13, wherein said material is selected from the group consisting of cellulose acetate butyrate, triacetate cellulose or glass.

15. An apparatus as claimed in claim 11, wherein said sample well is substantially cylindrical in shape and said optical window element is substantially in the form of a circular disk coaxially receivable within said sample well, and wherein said opening comprises an annular gap between the outer periphery of said window element and confronting interior wall surfaces of said sample well.

16. An apparatus as claimed in claim 15, wherein said closure device comprises an annular seal for sealing said annular gap, said annular seal being frictionally receivable within said sample well and having a central aperture for exposing a corresponding central portion of said window element.

17. An apparatus as claimed in claim 11, further comprising at least one spacer disposed in said sample well for maintaining the bottom surface of said window element in said opposed, spaced-apart relationship with the bottom wall surface of said sample well.

18. An apparatus as claimed in claim 11, wherein said sample well comprises one of a plurality of connected sample wells which are substantially identical to each other, each of said sample wells being provided with one of said window elements, one of said openings, one of said dried nucleic acid amplification reagents, and one of said dried nucleic acid assay reagents.

19. A method for carrying out an integrated nucleic acid amplification and homogeneous nucleic acid fluorescence polarization assay on a liquid biological sample, comprising the steps of:

providing a sample well having a substantially flat, upwardly facing, bottom interior surface;

inserting into said sample well an optical window element having a circumferential edge and a substantially flat, downward facing bottom surface;

maintaining the bottom surface of said optical window element in opposed, spaced-apart relationship with the bottom interior surface of said sample well to define a capillary chamber therebetween;

introducing a liquid biological sample into said capillary chamber through an opening between the circumferential edge of said optical window element and a confronting interior side wall surface of said sample well;

bringing said liquid biological sample into contact with a dried nucleic acid amplification reagent and a dried homogeneous nucleic acid fluorescence polarization assay reagent in said capillary chamber;

sealing said opening;

incubating said sample well to allow said liquid biological sample to react with said nucleic acid amplification reagent and said nucleic acid fluorescence polarization assay reagent; and detecting fluorescence polarization in said liquid biological sample through said optical window element.

20. A method as claimed in claim 19, wherein said optical window element is made of a material that does not interfere with the transmission of polarized light, and wherein the step of detecting fluorescence polarization in said liquid biological sample comprises directing polarized light through said optical window element.

21. A method as claimed in claim 19, wherein said optical window element is made of a light-polarizing material, and wherein the step of detecting fluorescence polarization in said liquid biological sample comprises directing unpolarized light through said optical window element.

* * * * *